US009379508B2

(12) United States Patent
Haarer et al.

(10) Patent No.: US 9,379,508 B2
(45) Date of Patent: Jun. 28, 2016

(54) IMPLANTABLE LEADS WITH A CONDUCTOR COIL HAVING TWO OR MORE SECTIONS

(71) Applicant: Cardiac Pacemakers, Inc., St. Paul, MN (US)

(72) Inventors: Joshua Haarer, Hugo, MN (US); Yevgenia Sheikholeslami, Minneapolis, MN (US); Patrick Willoughby, Hugo, MN (US); Andrew L. De Kock, Andover, MN (US); Kimberly A. Morris, Minneapolis, MN (US); Benjamin J. Haasl, Forest Lake, MN (US); Brian L. Schmidt, White Bear Lake, MN (US); Emilio Abner Avilés Delgado, Dorado, PR (US); Fabian E. Morales-Ortiz, Toa Baja, PR (US); Ronald W. Kunkel, Jim Falls, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 149 days.

(21) Appl. No.: 13/944,218

(22) Filed: Jul. 17, 2013

(65) Prior Publication Data
US 2014/0075753 A1 Mar. 20, 2014

Related U.S. Application Data

(62) Division of application No. 12/979,911, filed on Dec. 28, 2010, now Pat. No. 8,494,651.

(60) Provisional application No. 61/291,151, filed on Dec. 30, 2009.

(51) Int. Cl.
*H01R 43/04* (2006.01)
*H01R 43/20* (2006.01)
*A61N 1/05* (2006.01)

(52) U.S. Cl.
CPC ............... *H01R 43/20* (2013.01); *A61N 1/056* (2013.01); *A61N 1/0587* (2013.01); *A61N 2001/0585* (2013.01); *Y10T 29/49117* (2015.01); *Y10T 29/49218* (2015.01)

(58) Field of Classification Search
CPC ...... A61N 1/056; A61N 1/0587; H01R 43/00; H01R 43/06; H01R 43/20; H01R 43/0221; Y10T 29/49117; Y10T 29/49002
USPC .......................................................... 29/882
See application file for complete search history.

(56) References Cited

U.S. PATENT DOCUMENTS 4,437,474 A * 3/1984 Peers-Trevarton ..... A61N 1/056
                                                     29/605
5,571,157 A * 11/1996 McConnell ............ A61N 1/057
                                                     607/116

(Continued)

FOREIGN PATENT DOCUMENTS

| JP | 2003515358 A | 5/2003 |
| JP | 2006524110 A | 10/2006 |
| WO | WO2007078360 A2 | 7/2007 |

OTHER PUBLICATIONS

International Search Report and Written Opinion Issued in PCT/US2010/062420, mailed Jun. 17, 2011, 16 pages.

*Primary Examiner* — Michael Kahelin
*Assistant Examiner* — Minh Duc Pham
(74) *Attorney, Agent, or Firm* — Faegre Baker Daniels LLP

(57) ABSTRACT

Various coiled conductors having two or more sections and methods and devices for constructing such conductors are disclosed. The various embodiments of coiled conductors and related methods include two or more sections that can have different mechanical, structural, and/or electrical characteristics.

11 Claims, 9 Drawing Sheets

(56) References Cited

U.S. PATENT DOCUMENTS

| | | |
|---|---|---|
| 5,800,496 A | 9/1998 | Swoyer et al. |
| 6,144,882 A | 11/2000 | Sommer et al. |
| 6,265,691 B1 * | 7/2001 | Cardineau ............... H02G 1/128 219/121.69 |
| 6,295,476 B1 | 9/2001 | Schaenzer |
| 6,373,024 B1 | 4/2002 | Safarevich et al. |
| 6,477,427 B1 * | 11/2002 | Stolz ....................... A61N 1/05 607/116 |
| 6,671,554 B2 | 12/2003 | Gibson et al. |
| 7,110,828 B2 | 9/2006 | Kolberg et al. |
| 7,474,924 B2 | 1/2009 | Honeck et al. |
| 7,486,994 B2 | 2/2009 | Zarembo et al. |
| 8,494,651 B2 | 7/2013 | Hearer et al. |
| 2004/0014355 A1 | 1/2004 | Osypka et al. |
| 2007/0142890 A1 | 6/2007 | Zarembo et al. |
| 2009/0149920 A1 | 6/2009 | Li et al. |
| 2010/0114275 A1 | 5/2010 | Min |
| 2011/0160825 A1 | 6/2011 | Haarer et al. |

* cited by examiner

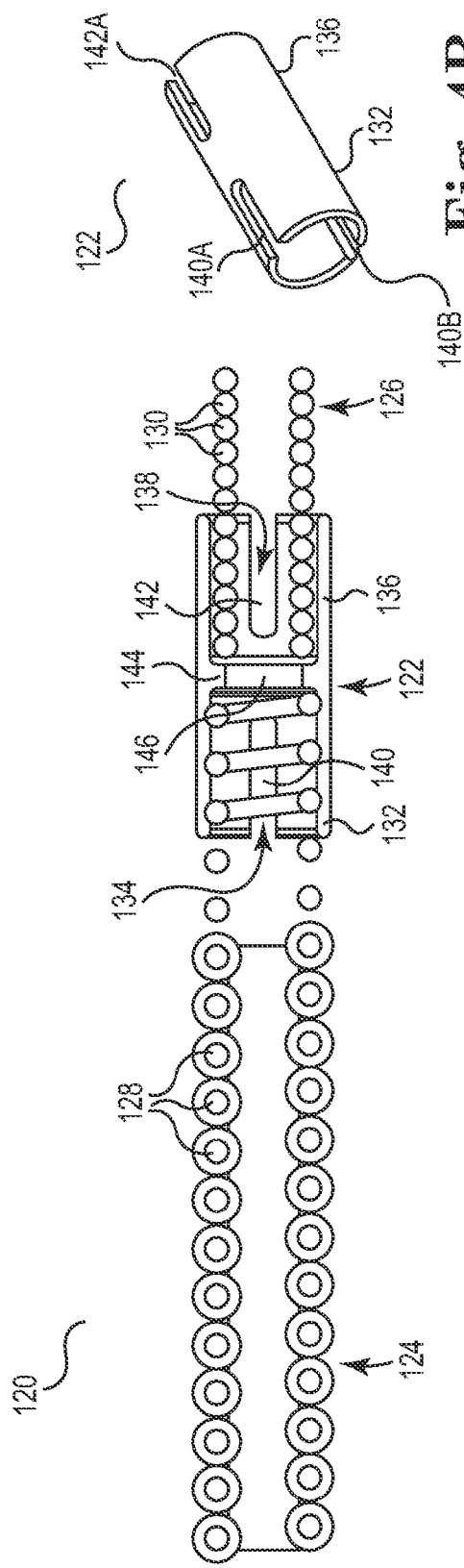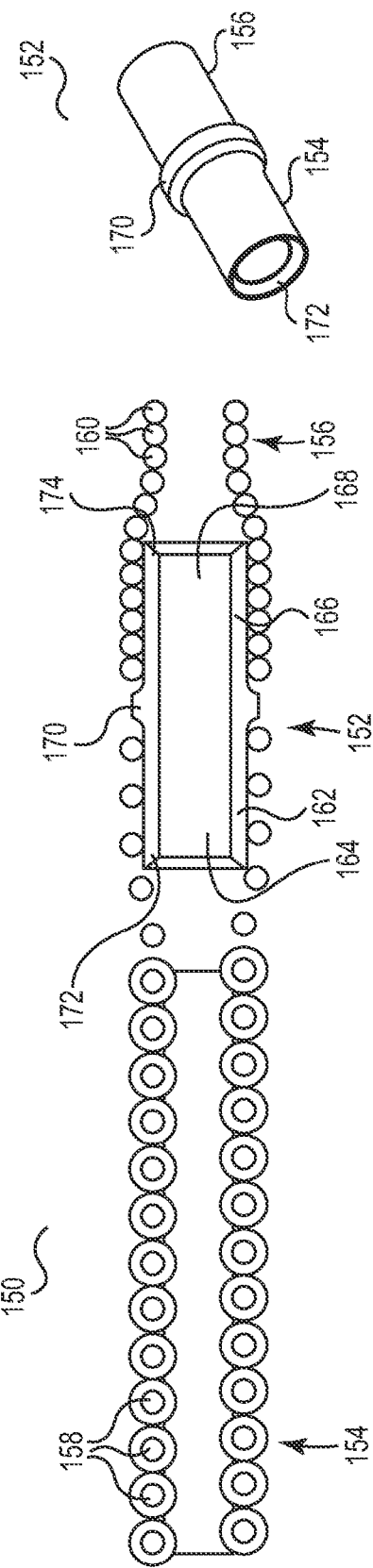

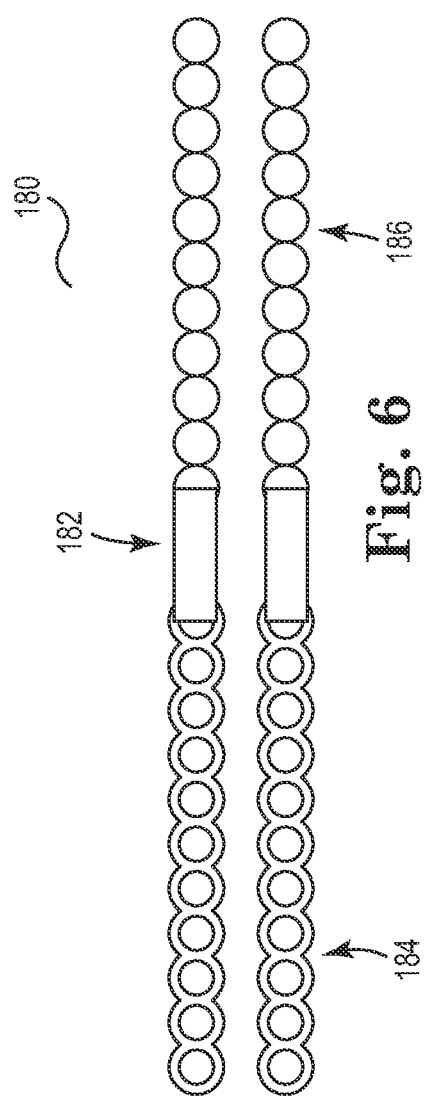
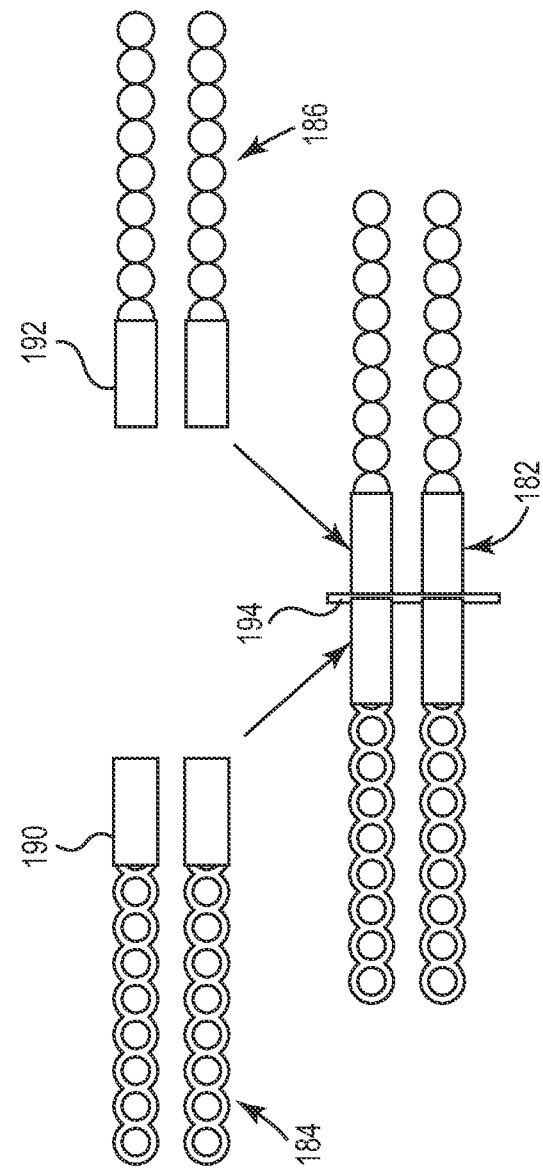

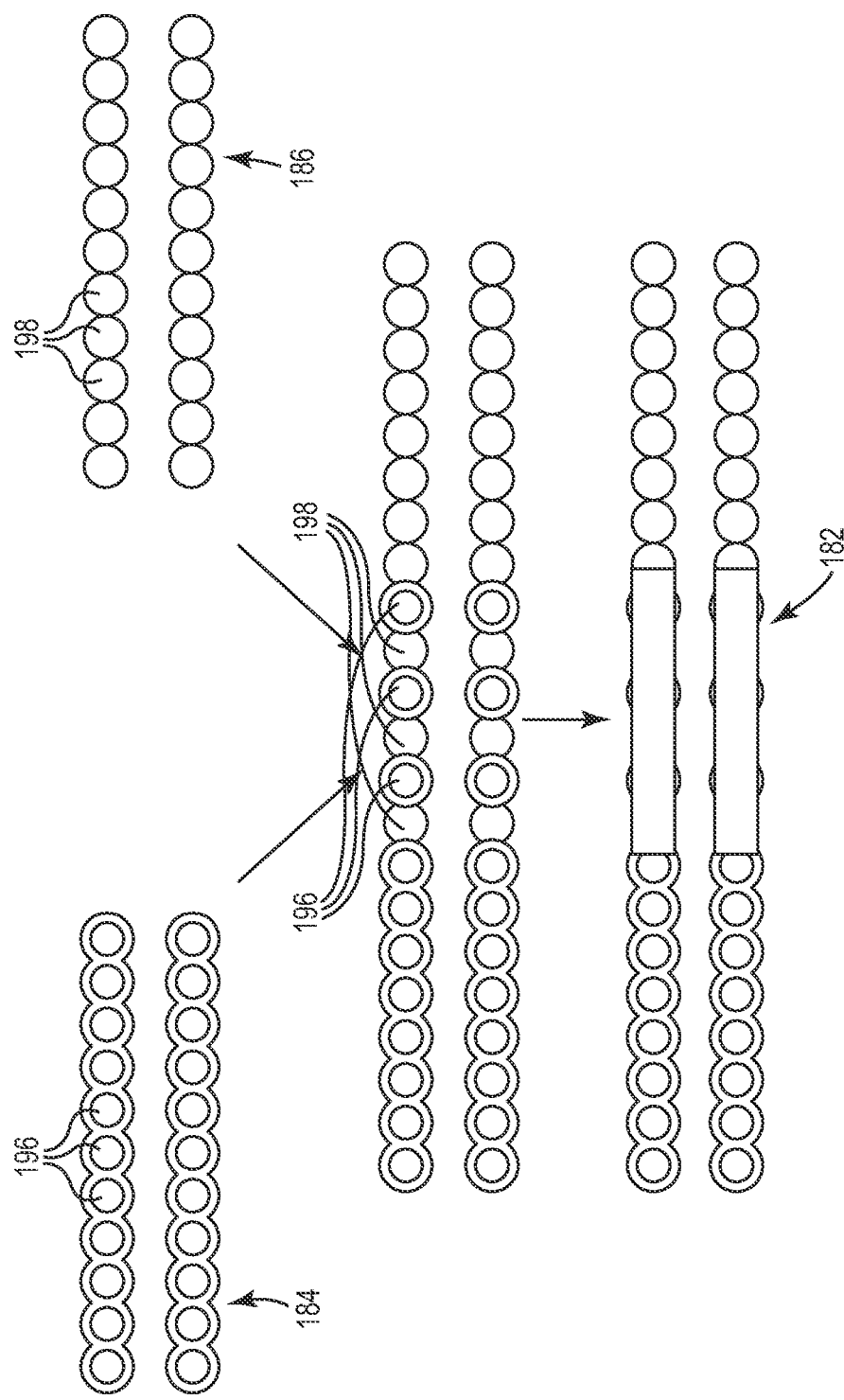

IMPLANTABLE LEADS WITH A CONDUCTOR COIL HAVING TWO OR MORE SECTIONS

CROSS-REFERENCE TO RELATED APPLICATION

This application is a division of U.S. application Ser. No. 12/979,911, filed Dec. 28, 2010, which claims priority under 35 U.S.C. §119 to U.S. Provisional Application No. 61/291,151, filed on Dec. 30, 2009, entitled "Implantable Leads with a Conductor Coil Having Two or More Sections," which is hereby incorporated herein by reference in its entirety for all purposes.

TECHNICAL FIELD

The various embodiments disclosed herein relate to body implantable medical devices for sensing electrical impulses and/or delivering electrical stimulation in a body, and more particularly, to methods and devices relating to a coiled conductor having at least two sections.

BACKGROUND

Various types of medical electrical leads for use in cardiac rhythm management systems are known. Such leads are typically extended intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explanation procedures. There is a continuing need for improved lead designs.

SUMMARY

Discussed herein are various coiled conductors for implantable medical electrical leads, including coiled conductors having two or more segments, as well as medical electrical leads including such conductors.

In Example 1, a medical lead comprises a lead body, at least one lumen disposed within the lead body, and a coiled conductor disposed within the lumen. The coiled conductor comprises a first coiled segment, a second coiled segment, and a junction member coupled to an end of the first and second coiled segments. The first coiled segment comprises a first number of filars and a first pitch and the second coiled segment comprises a second number of filars and a second pitch.

Example 2 relates to the medical lead according to Example 1, wherein the first coiled segment further comprises a first outer diameter and a first inner diameter and the second coiled segment further comprises a second outer diameter and a second inner diameter.

Example 3 relates to the medical lead according to either Example 1 or 2, wherein the first outer diameter is greater than the second outer diameter and the first inner diameter is greater than the second inner diameter.

Example 4 relates to the medical lead according to any of Examples 1-3, wherein the first number of filars is less than the second number of filars.

Example 5 relates to a medical lead according to any of Examples 1-4, wherein the first coiled segment comprises coated filars and the second coiled segment comprises uncoated filars.

Example 6 relates to a medical lead according to any of Examples 1-5, wherein the first coiled segment is a first coiled conductor and the second coiled segment is a second coiled conductor.

Example 7 relates to a medical lead according to any of Examples 1-6, wherein the junction member is a weld zone.

Example 8 relates to a medical lead according to any of Examples 1-6, wherein the junction member is a junction ring.

Example 9 relates to a medical lead according to Example 8, wherein the junction ring comprises a male coupling component configured to be disposed within a lumen at the end of the first coiled segment and a female coupling component comprising a lumen configured to receive the end of the second coiled segment.

Example 10 relates to a medical lead according to Example 8, wherein the junction ring comprises a first female coupling component comprising a lumen configured to receive the end of the first coiled segment and a second female coupling component comprising a lumen configured to receive the end of the second coiled segment.

Example 11 relates to a medical lead according to Example 8, wherein the junction ring comprises a first male coupling component configured to be disposed within a lumen at the end of the first coiled segment and a second male coupling component configured to be disposed within a lumen at the end of the second coiled segment.

According to Example 12, a medical lead comprises a lead body, at least one lumen disposed within the lead body, and a coil conductor disposed within the lumen. The coil conductor comprises a proximal coiled segment, a distal coiled segment, and a junction member coupled to the distal end of the proximal coiled segment and the proximal end of the distal coiled segment. The proximal segment comprises a first number of coated filars, a first pitch, and a first outer diameter. The distal segment comprises a second number of uncoated filars, a second pitch, and a second outer diameter that is less than the first outer diameter.

Example 13 relates to a medical lead according to Example 12, wherein the junction member is a weld zone.

Example 14 relates to a medical lead according to Example 12, wherein the junction member is a junction ring comprising a male coupling component configured to be disposed within a lumen at the distal end of the proximal coiled segment and a female coupling component comprising a lumen configured to receive the proximal end of the distal coiled segment.

According to Example 15, a method of constructing a coil conductor having at least a first segment and a second segment comprises winding a first number of at least one filars into a coiled configuration over a first section of a mandrel to form the first segment and winding a second number of at least one filars beginning at the transition point into a coiled configuration over a second section of the mandrel to form the second segment. The winding to form the first segment ends at a transition point. The first section has a first outer diameter and the second section has a second outer diameter. The first segment includes the first number of at least one filars, a first pitch, and a first inner diameter. The second segment has the second number of at least one filars, a second pitch, and a second inner diameter. At least one of the first number of filars, the first pitch, the first inner diameter, and the first outer diameter is different from at least one of the second number of filars, the second pitch, the second inner diameter, and the second outer diameter.

Example 16 relates to a medical lead according to Example 15, wherein the at least one filar is a coated filar and wherein the method further comprises removing the coating while winding the at least one filar to form either the first segment or the second segment, whereby one of the first and second segment is uncoated.

Example 17 relates to a medical lead according to Example 15 or 16, and further comprises removing one of the first number of filars at the transition point before winding the second number of filars, whereby the second number of filars is less than the first number of filars.

Example 18 relates to a medical lead according to Example 15 or 16, and further comprises adding a filar at the transition point before winding the second number of filars, whereby the second number of filars is greater than the first number of filars.

Example 19 relates to a medical lead according to any of Examples 15-18, wherein the second outer diameter of the mandrel is smaller than the first outer diameter of the mandrel.

Example 20 relates to a medical lead according to any of Examples 15-19 and further comprises winding a third number of the at least one filars beginning at a second transition point into a coiled configuration over a third section of the mandrel to form a third segment, wherein the third section comprises a third outer diameter and the third segment comprises the third number of at least one filars, a third pitch, and a third inner diameter, wherein at least one of the second number of filars, the second pitch, the second inner diameter, and the second outer diameter is different from at least one of the third number of filars, the third pitch, the third inner diameter, and the third outer diameter.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4A is a schematic cross-section drawing of a coiled conductor with a junction ring, according to another embodiment.

FIG. 4B is a perspective view of the junction ring of FIG. 4A, according to one embodiment.

FIG. 5A is a schematic cross-section drawing of a coiled conductor with a junction ring, according to yet another embodiment.

FIG. 5B is a perspective view of the junction ring of FIG. 5A, according to one embodiment.

FIG. 6 is a schematic view of a portion of a coiled conductor with a weld zone, according to one embodiment.

FIG. 7A is a schematic view of one method of creating a coiled conductor with a weld zone, according to one embodiment.

FIG. 7B is a schematic view of another method of creating a coiled conductor having a weld zone, according to another embodiment.

Figure 1A:
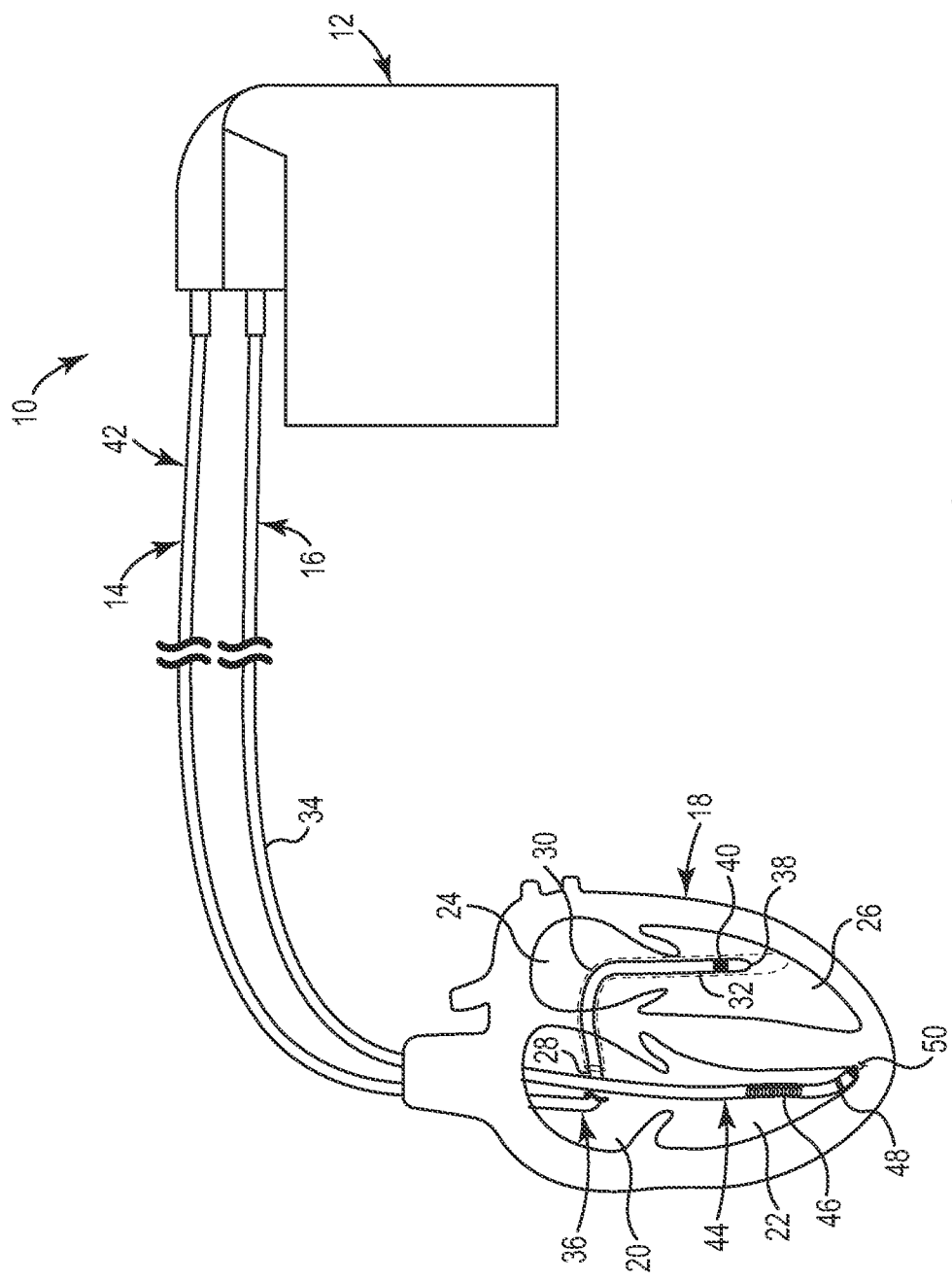
FIG. 1A is a schematic drawing of a cardiac rhythm management system including a pulse generator coupled to a pair of medical electrical leads deployed in a patient's heart, according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The various embodiments disclosed herein relate to a coiled wire conductor for use in a medical electrical lead and related methods and devices for manufacturing the conductor. The leads according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate bi-ventricular pacing in a CRT or CRT-D system. Still additionally, leads formed according to embodiments of the present invention may be configured to be secured to an exterior surface of the heart (i.e., as epicardial leads). FIG. 1A is a schematic drawing of a cardiac rhythm management system 10 including a pulse generator 12 coupled to a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30.

According to one embodiment, as shown in FIG. 1A, lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes a distal end 38 and an electrode 40 both positioned within the branch vessel 32. The illustrated position of the lead 14 may be used for delivering a pacing and/or defibrillation stimulus to the left side of the heart 18. Additionally, it will be appreciated that the lead 14 may also be partially deployed in other regions of the coronary venous system, such as in the great cardiac vein or other branch vessels for providing therapy to the left side or right side of the heart 18.

In the illustrated embodiment, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown in FIG. 1A, in the illustrated embodiment, the lead 16 includes a proximal portion 34 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. As will be appreciated, the high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

In various embodiments, the lead 16 includes additional defibrillation/cardioversion and/or additional pace/sense electrodes positioned along the lead 16 so as to provide multipolar defibrillation/cardioversion capabilities. In one exemplary embodiment, the lead 16 includes a proximal high voltage electrode in addition to the electrode 46 positioned along the lead 16 such that it is located in the right atrium 20 (and/or superior vena cava) when implanted. As will be appreciated, additional electrode configurations can be utilized with the lead 16. In short, any electrode configuration can be employed in the lead 16 without departing from the intended scope of the present invention.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter defibrillator (ICD), a cardiac resynchronization (CRT) device configured for bi-ventricular pacing, and/or includes combinations of pacing, CRT, and defibrillation capabilities.

Figure 1B:
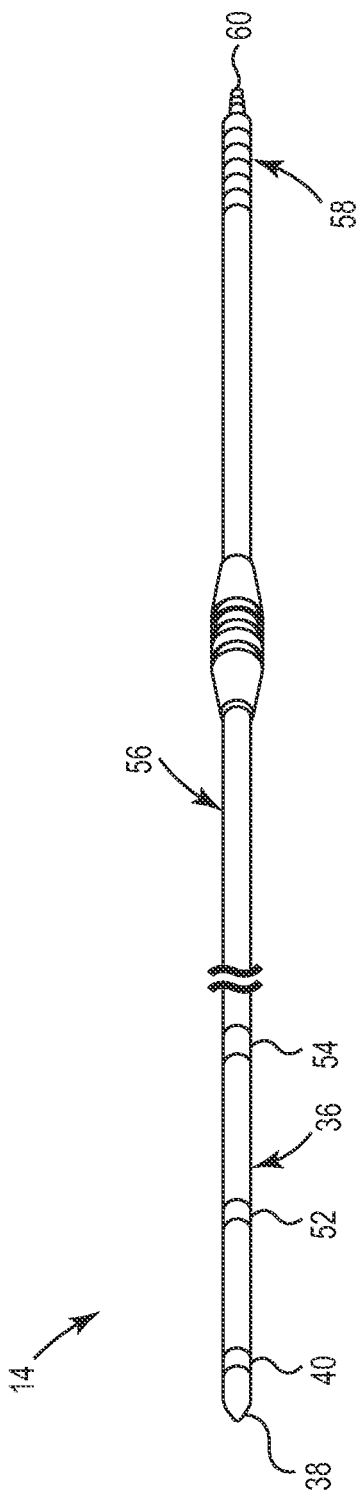
FIG. 1B is a perspective view of one of the leads shown in FIG. 1, according to one embodiment.

FIG. 1B is a perspective view of the lead 14 shown in FIG. 1A. As discussed above, the lead 14 is adapted to deliver electrical pulses to stimulate a heart and/or for receiving electrical pulses to monitor the heart. The lead 14 includes an elongated polymeric lead body 56, which may be formed from any polymeric material such as polyurethane, polyamide, polycarbonate, silicone rubber, or any other suitable polymer.

In addition, the lead 14 can have one electrode 40 as shown in FIG. 1A, or the lead 14 may have more than one electrode as shown in FIG. 1B, in which the lead 14 has three electrodes 40, 52, 54 along its distal section 36.

As further shown in FIG. 1B, the lead 14 further includes a connector 58 operatively associated with the proximal end of the lead body 56. The connector 58 is configured to mechanically and electrically couple the lead 14 to the pulse generator 12 as shown in FIG. 1A, and may be of any standard type, size or configuration. The connector 58 has a terminal pin 60 extending proximally from the connector 58. As will be appreciated, the connector 58 is electrically and mechanically connected to the electrodes 40, 52, 54 by way of one or more conductors (not shown) that are disposed within an elongate tubular member 62 within the lead body 56 (as best shown in FIG. 1C).

Figure 1C:
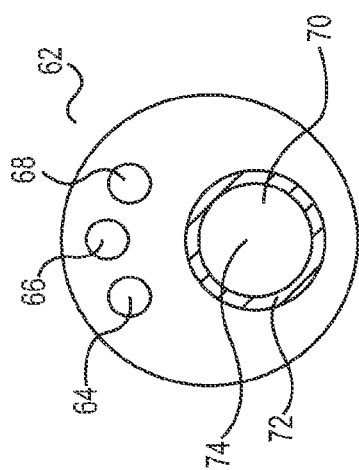
FIG. 1C is a schematic cross-section drawing of a portion of a lead, according to one embodiment.

In various embodiments, the elongate tubular member 62 depicted in cross section in FIG. 1C defines multiple lumens (and is also referred to herein as a "multilumen tube"). In some implementations, the multilumen tube 62 forms a central or inner portion of the lead body 56 and extends from a proximal portion to a distal portion of the body 56. As shown, in some embodiments the multilumen tube 62 has four lumens 64, 66, 68, 70. In other embodiments, the multilumen tube 62 has a single lumen, two or more lumens, three or more lumens, four or more lumens, or any other suitable number of lumens. Further, in some embodiments one or more of the lumens are offset from the longitudinal axis of the multilumen tube 62. For example, the first lumen 64 has a longitudinal axis that is non-coaxial with respect to the longitudinal axis of the multilumen tube 62.

As mentioned above, in some embodiments the lumens 64, 66, 68, 70 provide a passageway through which conductors can pass and electrically connect one or more of electrodes 40, 52, 54 to the connector 58. The conductors utilized may take on any configuration providing the necessary functionality. For example, as will be appreciated, the conductor coupling the electrode 40 to the connector 58 (and thus, to the pulse generator 12) may be a coiled conductor defining an internal lumen for receiving a stylet or guidewire for lead delivery. As best shown as an example in FIG. 1C, conductor 72 disposed in lumen 70 is an example of a coiled conductor 72 defining an internal lumen 74 within the conductor 72. Conversely, in various embodiments, any of the conductors to any of the electrodes 40, 52, 54 may be multi-strand cable conductors.

Figure 2A:
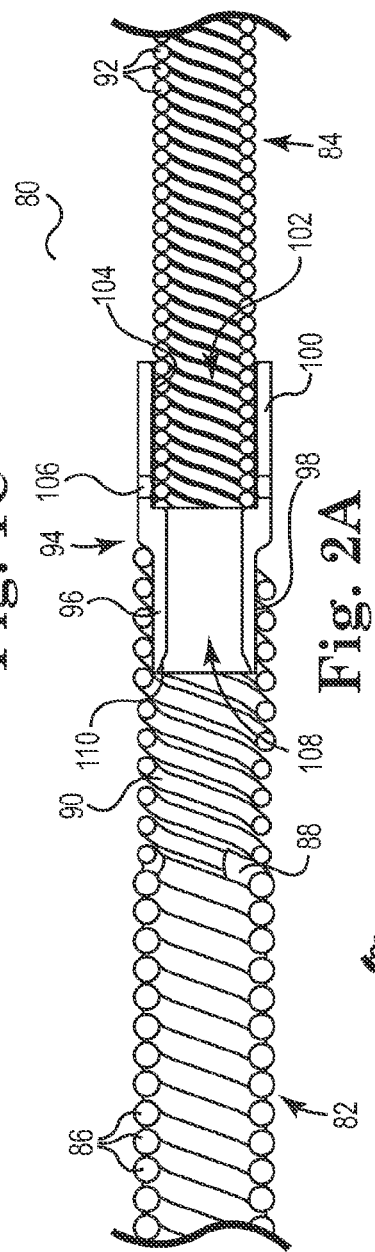
FIG. 2A is a schematic cross-section drawing of a coiled conductor with a junction ring, according to one embodiment.
Figure 2B:
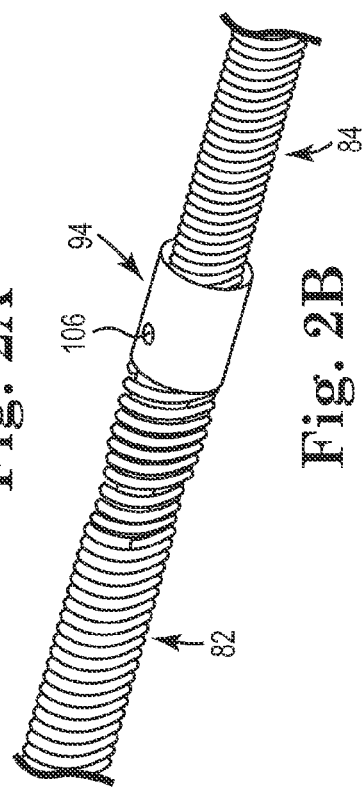
FIG. 2B is a perspective view of the coiled conductor of FIG. 2A, according to one embodiment.

FIGS. 2A and 2B depict a coiled conductor 80 according to one embodiment. The conductor 80 has a proximal coil 82 and a distal coil 84 that are coupled via a joint member 94. In the embodiment depicted in FIGS. 2A and 2B, the joint member 94 is a joint ring 94.

"Joint ring" is intended for purposes of this application to mean any coupling component, structure, or device that is configured to mechanically and electrically couple two coiled conductors or coiled conductor segments in series. It is understood that any coiled conductor embodiment disclosed herein has at least two segments or sections, wherein "segment" and "section" are intended to be used interchangeably for purposes of this application. In some implementations, each of the sections or segments is a separate conductor coil. In alternative embodiments, the sections or segments are part of the same coil.

In the embodiment shown in FIGS. 2A and 2B, the joint ring 94 has a male member 96 which is positioned within the lumen of the conductor 82. The outer surface 98 of the male member 96 is in contact with the filars 86 at the distal end of the coiled conductor 82, thereby resulting in a mechanical and electrical connection.

Figure 3A:
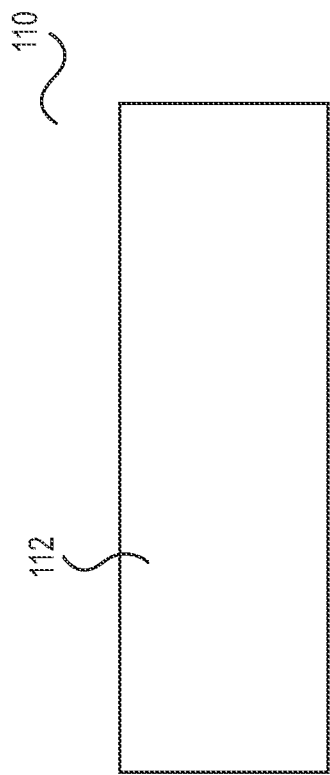
FIG. 3A is a side view of an attachment tube, according to one embodiment.
Figure 3B:
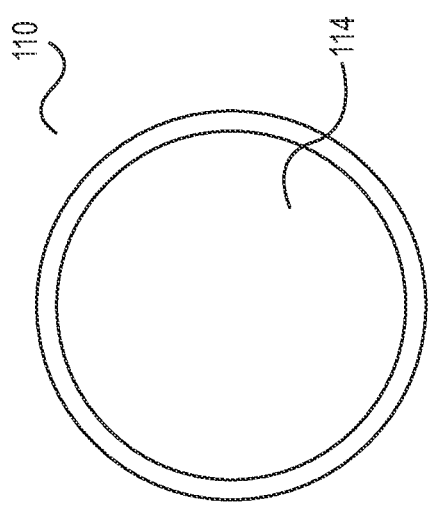
FIG. 3B is a cross-sectional view of the attachment tube of FIG. 3A, according to one embodiment.

According to one implementation, at least one of the filars 86 positioned on the male member 96 is welded or soldered or otherwise attached to the member 96, thereby attaching the conductor 82 to the joint ring 94. Alternatively, the filars 86 are attached to the male member 96 by positioning an attachment tube 110 (as shown in FIGS. 3A and 3B) over the filars 86 and the male member 96, thereby resulting in the filars 86 being disposed between the male member 96 and the attachment tube 110. The tube has a body 112 and an inner lumen 114 and in this embodiment is sized to be disposed over the male member 96 and also over the filars 86 that are positioned over the male member 96. In one embodiment, once the tube 110 is in position over the male member 96 and filars 86, the tube 110 is crimped or otherwise tightened against the filars 86 and member 96, thereby attaching the filars 86 to the member 96. In a further alternative, any form of mechanical attachment can be used to attach the conductor 82 to the ring 94.

The ring 94 also has a female member 100 defining a lumen 102 that has an inner surface 104. In the embodiment of FIGS. 2A and 2B, the proximal end of the coiled conductor 84 is positioned in the lumen 102, resulting in the individual filars 92 at the proximal end of the coiled conductor 84 being in contact with the inner surface 104 of the lumen 102, thereby resulting in a mechanical and electrical connection between the coiled conductor 84 and the joint ring 94.

In accordance with some implementations, the at least one of the filars 92 positioned inside the lumen 102 is welded to the female member 100, thereby attaching the conductor 84 to the ring 94. In one exemplary embodiment, the welding can be accomplished using the aperture 106 in the outer wall of the female member 100. Alternatively, the filars 92 are attached to the female member 100 by inserting an attachment tube into the lumen 102 formed by the female member 100 and the filars 92. According to one embodiment, the attachment tube 110 depicted in FIGS. 3A and 3B can be one example of the attachment tube used with the female member 100. In this embodiment, the attachment tube 110 is sized to fit within the lumen 102 and also within the lumen formed by the filars 92 disposed within the lumen 102, thereby resulting in the filars 92 being disposed between the female member 100 and the attachment tube 110. In one embodiment, once the tube 110 is in position in the lumen 102, the female member 100 is crimped or otherwise tightened against the filars 86 and tube 110, thereby attaching the filars 86 inside the lumen 102 of the female member 100. In a further alternative, any form of mechanical attachment can be used to attach the conductor 84 to the ring 94.

In this embodiment, the male member 96 of the ring 94 defines a lumen 108 that is in communication with the lumen 102 of the female member 100, resulting in a ring 94 having a lumen that extends through the entire ring 94. In addition, as best shown in FIG. 2A, in certain implementations of the ring 94, the inner diameter of the lumen 102 is greater than the inner diameter of the lumen 108, thereby allowing additional space in the lumen 102 for the filars 92 of the coil 84. In fact, in certain embodiments such as that depicted in FIG. 2A, the difference in the diameters of the two lumens 102 and 108 is substantially equal to the outer diameter of the filars 92 of the coil 84, thereby allowing for the positioning of the filars 92 in the lumen 102 without impacting the resulting inner diameter through the lumens 102, 108, which remains substantially the same. As such, this lumen 102, 108 allows for use of the joint ring 94 without disrupting the lumen defined through the entire length of the coupled coils 82, 84 or coil segments 82, 84. In other words, the coupled coils 82, 84 with the ring 94 still have a lumen through which any guidewire or stylet or other similar device can be inserted without any type of physical blockage or impediment.

According to one embodiment, the ring 94 also has an additional feature that allows for easy insertion of a stylet or other similar component into and through the lumen 108 in the ring 94. That is, the ring 94 has a lip 110 defined at the opening of the lumen 108 that can guide any inserted elongated device being inserted through coil 82 and into coil 84 through the guide ring 94 without impeding the progress of the device.

While the embodiment of the ring 94 depicted in FIGS. 2A and 2B show the ring 94 disposed such that the male member 96 is disposed to receive the proximal coil 82 and the female member 100 is disposed to receive the distal coil 84, it is understood that the ring 94 can also be configured such that the male member 96 receives the distal coil and the female member 100 receives the proximal coil. The depicted configuration in FIGS. 2A and 2B is exemplary and is not intended to be limiting with respect to whether the male member 96 or female member 100 is positioned toward the proximal coil or the distal coil.

In alternative embodiments, the joint ring can have two male members or two female members, depending on the design requirements of the particular coil conductor or lead. For example, FIGS. 4A and 4B depict a conductor coil 120 having a joint ring 122 with two female members 132, 136. The end of the first coiled conductor 124 is disposed within the lumen 134 of the first female member 132, and the end of the second coiled conductor 126 is disposed within the lumen 138 of the second female member 136.

Similarly to the ring 94 in FIGS. 2A and 2B, the inner diameters of the lumens 134, 138 in various embodiments of the ring 122 can be configured to provide for a substantially uniform inner diameter across both lumens 134, 138 regardless of any difference between the outer diameters of the filars 128, 130 of the two coils 124, 126. In other words, the inner diameters of the two lumens 134, 138 can vary depending on the thickness of the filars of the coils 124, 126 that the ring 122 is intended to couple to ensure that the inner diameter of the lumens 134, 138 remains substantially uniform, thereby allowing for easy insertion of a stylet or other similar device through the coil 120.

In accordance with one embodiment, the ring 122 has an inner shoulder 144 disposed between the two lumens 134, 138. The shoulder 144 can serve to separate the first lumen 134 from the second lumen 138 and defines a lumen 146 that is substantially equal to the inner diameters of the lumens 134, 138 when the coils 124, 126 are positioned therein. In other words, the lumen 146 must have an inner diameter at least as large as the inner diameters of the lumens 134, 138 when those lumens contain the coils 124, 126 in order to ensure that any stylet or other such device can be inserted through the ring 122. In addition, according to certain embodiments, the shoulder 144 can help to position the coils 124, 126 to ensure that the appropriate amount of each coil 124, 126 is positioned in each lumen 134, 138 to achieve an appropriate mechanical and/or electrical connection with the ring 94.

According to one implementation, the ring 122 has two slots 140, 142 disposed in the outer walls of the two female members 132, 136. Each of the slots 140, 142 are provided to simplify the welding of the filars 128, 130 of the two coils 124, 126 to the inner surfaces of the respective lumens 134, 138. That is, the slots 140, 142 make it easier to weld the filars 128, 130 inside the lumens 134, 138 from a position outside of the ring 122 by providing physical and visual access through the slots 140, 142 to those filars 128, 130 disposed inside the lumens 134, 138. In the embodiment as best shown in FIG. 4B, each of the two female members 132, 136 can have two slots, with the first member 132 having two slots 140A, 140B and the second member 136 having two slots 142A, 142B (not visible in the figure). Alternatively, each member 132, 136 may have only one slot or no slot.

The coiled conductor 150 according the embodiment depicted in FIGS. 5A and 5B has a joint ring 152 having two male members 162, 166. The end of the first coiled conductor 154 is disposed over the first male member 162, and the end of the second coiled conductor 156 is disposed over the second male member 166. In addition, in this implementation, the openings of the lumens 164, 168 both have lips 172, 174 that can guide any elongated device being inserted through the ring 152 in either direction without impeding the progress of the device.

In accordance with one embodiment, the ring 152 has an outer shoulder 170 disposed on the outer surface of the ring 152 between the two male members 162, 166. The shoulder 170 can serve to separate the first member 162 from the second member 166 and has an outer diameter that can be configured to fit within the lumen of the lead in which the coil 150 is to be positioned. In addition, according to certain embodiments, the shoulder 170 can help to position the first and second coiled conductors 154, 156 to ensure that the appropriate amount of each conductor 154, 156 is positioned on each member 162, 166 to achieve an appropriate mechanical and/or electrical connection with the ring 152.

In alternative embodiments, other forms of coupling components can be used to couple two or more coiled segments in series. For example, the two or more coiled segments can be coupled together by any one of several welding processes. FIG. 6 depicts a specific example of a coiled conductor 180 having a joint member 182 that is a weld zone 182. That is, the first coiled conductor 184 and the second coiled conductor 186 are welded together at their respective ends to create a single coiled conductor 180 having a weld zone. "Weld zone" is intended for purposes of this application to mean any coupling component that is created between two coiled conductors or coiled conductor segments based on a welding process without any separate mechanical coupling device or component.

Figure 7C:
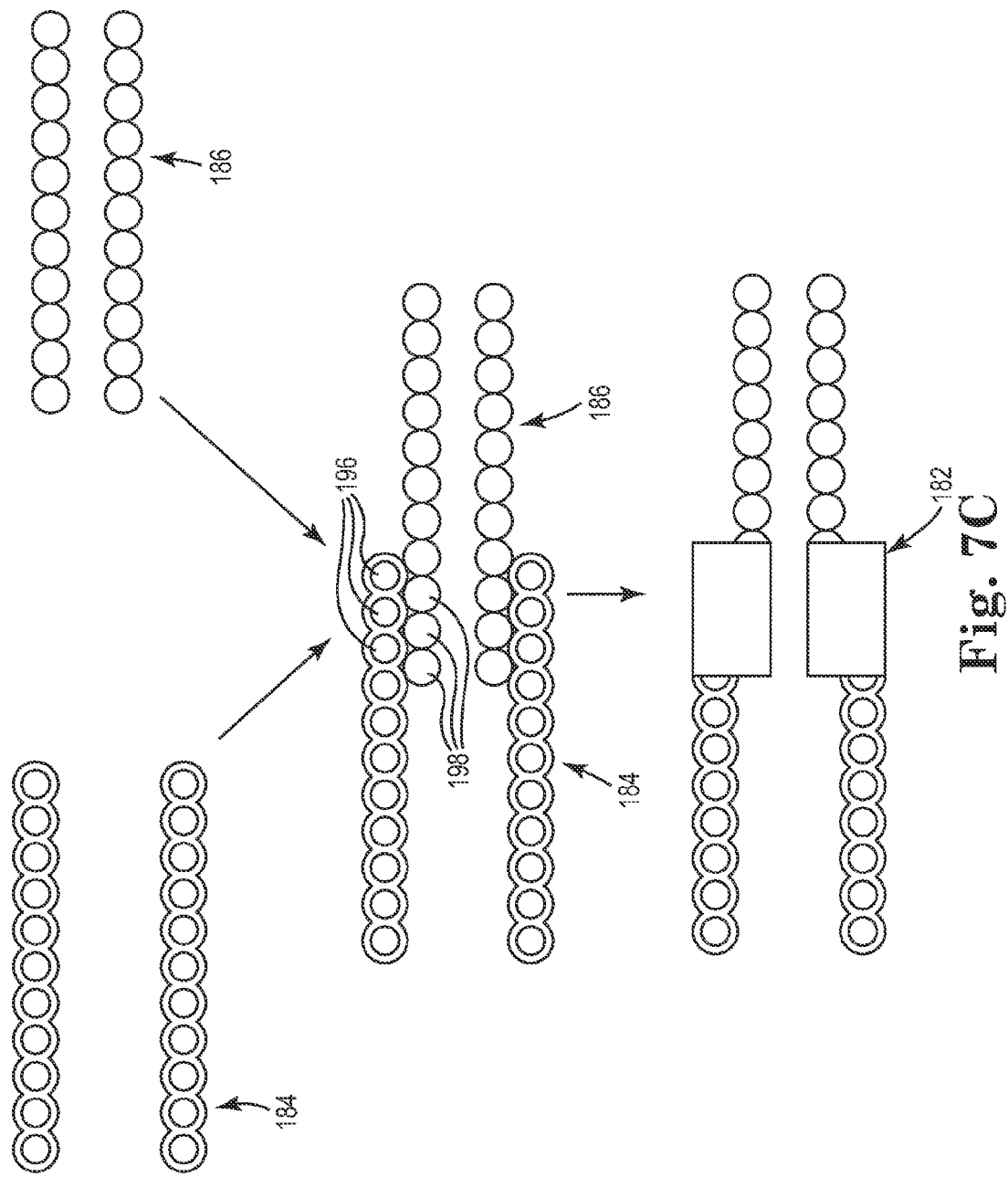
FIG. 7C is a schematic view of still another method of creating a coiled conductor having a weld zone, according to still another embodiment.

A weld zone such as the zone 182 in FIG. 6 can be created using several different methods, such as those depicted in FIGS. 7A, 7B, and 7C.

FIG. 7A depicts a method of creating a weld zone according to one implementation in which two weld bands are created at the ends of the coil segments and then welded together. In this implementation, the two weld bands 190, 192 are first created by welding together the filars at one end of each of the first coiled conductor 184 and the second coiled conductor 186. Once the weld bands 190, 192 are formed on the end of each conductor 184, 186, the two bands are then welded together to form the weld zone 182. In one embodiment, the two bands 190, 192 are welded together using a seam weld 194. Alternatively, any method of welding the two bands 190, 192 together can be used.

FIG. 7B depicts another method of creating the weld zone 182 coupling the two conductors 184, 186, according to another embodiment. In this embodiment, the filars 196 of the first conductor 184 are first intertwined with the filars 198 of the second conductor 186, such that the filars 196, 198 are combined together in series in a repeating fashion as shown in the figure. Once the filars 196, 198 are intertwined, the weld zone 182 is then created by welding the intertwined filars 196, 198 together.

FIG. 7C depicts yet another method of creating the weld zone 182 coupling the two conductors 184, 186, according to a further implementation. In this embodiment, the filars of one conductor are overlapped with the filars of the other conductor. In the example shown in FIG. 7C, the filars 198 at one end of the second coiled conductor 186 are overlapped with and disposed within the filars 196 at one end of the first coiled conductor 184. Alternatively, the filars 196 of the first coiled conductor 184 can be overlapped with and disposed within the filars 198 of the second coiled conductor 186. Once they are overlapped, the filars 196, 198 can be welded together to create the welded zone 182. It is understood that in some embodiments such as that shown in FIG. 7C, one coiled conductor may have a larger I.D. and O.D. than the other (such as, for example, the first conductor 184 having a larger I.D. and O.D. than the second 186 in the figure), thereby resulting in easy insertion of one set of filars into the other. On the other hand, it is not a requirement that the coiled conductors having different I.D.s and O.D.s.

Combining different conductor coils or conductor coil segments in series using a coupling component such as any of the various embodiments described herein (including the various joint rings and welding zones as described above) allows for creating or having a coil conductor that can exhibit widely different characteristics based on the different portions or sections along the length of the conductor. That is, a conductor coil can be constructed with two or more sections having different characteristics that provide for optimal functional performance needs of the conductor.

In one example, it may be desirable that one or more sections of a conductor coil are coated while one or more other sections are not. Returning to FIG. 2A, the individual filars 86 of the proximal conductor 82 are coated with an insulation coating 88. In one embodiment, the coating is ETFE. Alternatively, the coating 88 can be silicone, polyurethane, PTFE, PET, FEP, or any other polymeric material that can be used as a filar coating, whether insulative or non-insulative. In a further alternative, the coating 88 can be any known material that can be used in a coiled conductor coating. In the various embodiments discussed herein, it is possible to have one or more coiled segments (such as segment 82 in FIG. 2A) along a coiled conductor while one or more other coiled segments are uncoated (such as segment 84 in FIG. 2A).

Other characteristics can also be varied by coil segment. For example, it may be desirable that one or more sections have filars that have larger outer diameters than the filars of one or more other sections of the same coiled conductor. As one example, the filars 86 of the proximal segment 82 of FIG. 2A are thicker than the filars 92 of the distal segment 84 as a result of the coating 88. Alternatively, uncoated filars of one segment can simply be thicker than uncoated filars of another segment.

In a further embodiment, it may desirable that one or more sections have filars having a different pitch than one or more other sections. For example, the filars 86 of the proximal segment 82 of FIG. 2A have a different pitch than the filars 92 of the distal segment as a result of the greater thickness of the filars 86. Alternatively, filars of one segment can simply have a different pitch than filars of another segment unrelated to any thickness differences.

In yet another embodiment, it may be desirable that one or more sections have filars made of a different material than one or more other sections. For example, in certain embodiments, the filars 86 of the proximal segment 82 of FIG. 2A could be made of a material that is more flexible than the material of the filars 92 of the distal segment 84. Alternatively, any material that is known to be used in coiled conductors could be used in any one or more coiled segments, and one or more other coiled segments could be made of any other of such materials, thus resulting in at least two segments having filars made of different materials. In a further alternative, the two or more segments can be made of the same material.

In further alternative implementations, it may be desirable that one or more sections have a particular number of filars that is different from one or more other sections. For example, in certain embodiments, the proximal coil 82 of FIG. 2A has four filars 86 while the distal coil 84 has five filars 92. Alternatively, the number of filars can differ between coiled segments or coiled conductors connected in series by any number of filars that are known to be used in a conductor coil.

Various other embodiments of conductor coils having two or more segments with different characteristics can be created using unique manufacturing methods. For example, according to one implementation, the conductor coil 220 depicted in FIG. 8 can be manufactured using a process that results in the coil 220 having a proximal segment 222 having five filars that each have an insulation coating and a distal segment 224 having five filars that are uncoated. Because they are not coated, the filars of the distal segment 224 have a smaller outer diameter than the filars of the proximal segment 222, thereby causing the distal coiled segment 224 to have a smaller inner diameter and a smaller outer diameter than the coiled proximal segment 222.

Figure 8:
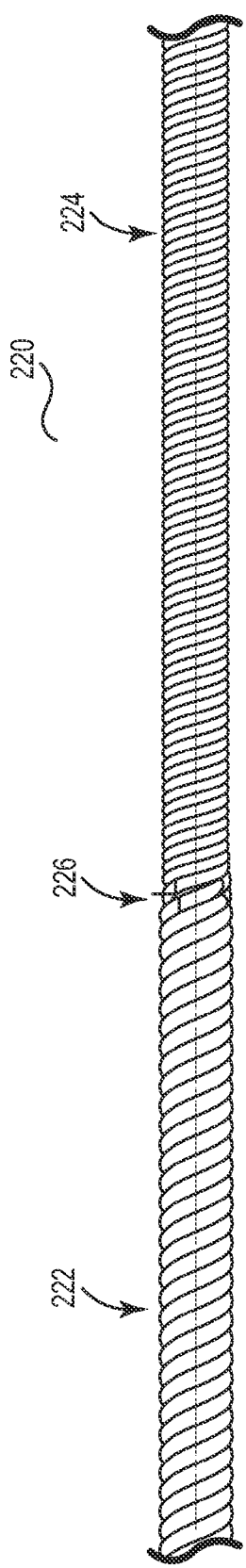
FIG. 8 is a side view of a portion of a coiled conductor having two segments, according to one embodiment.

The method, according to one implementation, begins by using a standard winding process to wind five coated filars into a coiled segment that will be the proximal coiled segment 222. In one embodiment, the five filars are formed into a coil using a mandrel having a first outer diameter that creates a coil having the desired inner diameter. When the winding process has created a proximal segment 222 of the predetermined length, a coating removal process is started to remove the coating from the filars. In one embodiment, the coating removal process is a laser ablation process using a laser such as an Excimer or $CO_2$ laser. Alternatively, any known coating removal process could be used. As shown in FIG. 8, the coating removal process results in a transition point 226 along the coil 220 at which the coated proximal section 222 ends and the uncoated distal section 224 begins. The combination winding and coating removal process continues until the end of the distal segment 224 of predetermined length is reached.

In accordance with one embodiment, the O.D. of the mandrel changes at the transition point 226 to a smaller O.D. In one implementation, this is because the five filars being wound to create the distal coil have a smaller thickness as a result of the removal of the coating, and thus a smaller O.D. is necessary in order to ensure that the five filars are wound tightly without any space between the filars.

Alternatively, any second O.D. could be used. That is, the process could include using a mandrel having a second O.D. that is smaller than the first to produce a distal coil with a smaller O.D. as described above, or the second O.D. could be larger than the first O.D. to produce a distal coil with a larger O.D. if that is desirable. In a further alternative, the distal coil could be wound with an O.D. that is the same as the O.D. of the proximal coil. In yet other alternatives, a mandrel having a third O.D. can be used to create a third segment of a different O.D., or a mandrel having additional segments having additional O.D.s could be used in any number to create any number of additional coiled segments.

It is understood that the above method could be performed in reverse. That is, the winding of the first segment could include a coating removal process to produce an uncoated segment, and then at the transition point, the coating removal process could be stopped and the second segment could be produced with a coating. It is further understood that any process similar to those described herein could be repeated several times to produce coils of not only two segments, but also three, four, or any number of segments having different characteristics.

In a further alternative, the coating removal process is performed prior to the winding process. That is, the coating is removed from each of the filars that are to be used in the coil prior to forming the filars into the coiled configuration. In some embodiments, the amount of coating that must be removed in order to create the uncoated segment of the predetermined length is calculated, and then that amount of coating is removed. In another embodiment, the filar is first cut to the predetermined appropriate length to create the coiled conductor of the desired length. It is understood that in embodiments in which there is more than one uncoated segment, the coating removal process is repeated for each of those segments.

In another alternative implementation, the coating removal process is performed after the winding process. That is, the coiled conductor is fully wound using a coated filar or two or more coated filars, and then the uncoated segment or segments are created by performing the coating removal process on the fully wound coil.

As discussed above with the coupling component embodiments, it can be desirable to have coiled segments with different numbers of filars. According to certain embodiments, the methods for manufacturing a conductor coil having two or more segments can also include methods for forming segments with different numbers of filars. More specifically, the methods disclosed herein include steps for winding a number of filars to form a coiled segment of a predetermined length and then either cutting one or more of those filars and continuing to wind such that the second segment has fewer filars, or adding one or more filars and continuing to wind such that the second segment has one or more additional filars.

In one embodiment in which the number of filars is reduced from the first segment to the second segment, the method includes starting with a predetermined number of filars that are wound into a coiled segment using a standard winding process with a mandrel. For purposes of this example, the predetermined number of filars is five, but it is understood that the first segment can have any known number of filars. When the winding process has created a first segment of the predetermined length, one of the filars is cut. In one embodiment, the end of the cut filar is then welded or otherwise attached by any known process to an adjacent filar. Alternatively, the cut filar is not attached. In a further alternative, two or more filars are cut. Regardless, the cutting of the filar results in a transition point along the coil at which the five filar segment ends and the four filar segment begins. The winding process then continues with four filars until the predetermined end of the second (four filar) segment. It is understood that at this point the winding process may be complete (in embodiments in which the coiled conductor has two segments) or it may continue with the addition or removal of one or more filars and the winding of a third segment, and perhaps subsequently the winding of additional segments as well.

It is understood that other parameters beyond the number of filars may be adjusted at the transition point as well. For example, if the number of filars is reduced at the transition point, the resulting second segment will have to have a smaller I.D. and O.D. if the individual loops of the coil contact each other with no spacing between each adjacent loop). As such, in one embodiment, the mandrel will have a transition point at the coil transition point at which the O.D. of the mandrel will decrease accordingly to produce a coiled configuration with the desired new O.D. and I.D.

In an alternative embodiment, the number of filars is increased between the winding of the first segment and the winding of the second segment. In this embodiment, the method includes starting with a predetermined number of filars that are wound into a coiled segment using a standard winding process with the mandrel having a predetermined O.D. For purposes of this example, the predetermined number of filars is four, but it is understood that the first segment can have any known number of filars. When the winding process has created a first segment of the predetermined length, an additional filar is added by inserting another wire into the winding process. In one embodiment, the additional wire is welded to an adjacent filar prior to beginning the winding of the second segment. Alternatively, the added filar is not attached. In a further alternative, two or more filars could be added. Regardless, the adding of the fifth filar results in a transition point along the coil at which the four filar segment ends and the five filar segment begins. The winding process then continues with five filars until the predetermined end of the second (five filar) segment. It is understood that at this point the winding process may be complete (in embodiments in which the coiled conductor has two segments) or it may continue with the addition or removal of one or more filars and the winding of a third segment, and perhaps subsequently the winding of additional segments as well.

As explained above, other parameters beyond the number of filars may be adjusted at the transition point as well. For example, in processes in which the number of filars is increased at the transition point as described in the previous paragraph and the first segment had no space between the individual loops of the coil, the resulting second segment will have to have a larger I.D. and O.D. as a result of the addition of one or more filars. As such, in one embodiment, the O.D. of the mandrel changes at the transition point to a larger O.D. that will produce a coiled configuration with the desired new O.D. and I.D.

The ability to manufacture or use coiled conductors having two or more segments with differing characteristics provides greater flexibility in the design of implantable medical leads. That is, a segmented coiled conductor allows for optimization of target lead characteristics and functional performance, such as set forth in the exemplary lead depicted in FIG. 9 and discussed below. Certain medical lead requirements can make it desirable for the lead to have different characteristics in different segments along the length of the lead. As such, a coiled conductor that has different segments with different characteristics along the length of the conductor can be used to optimize such requirements.

Figure 9:
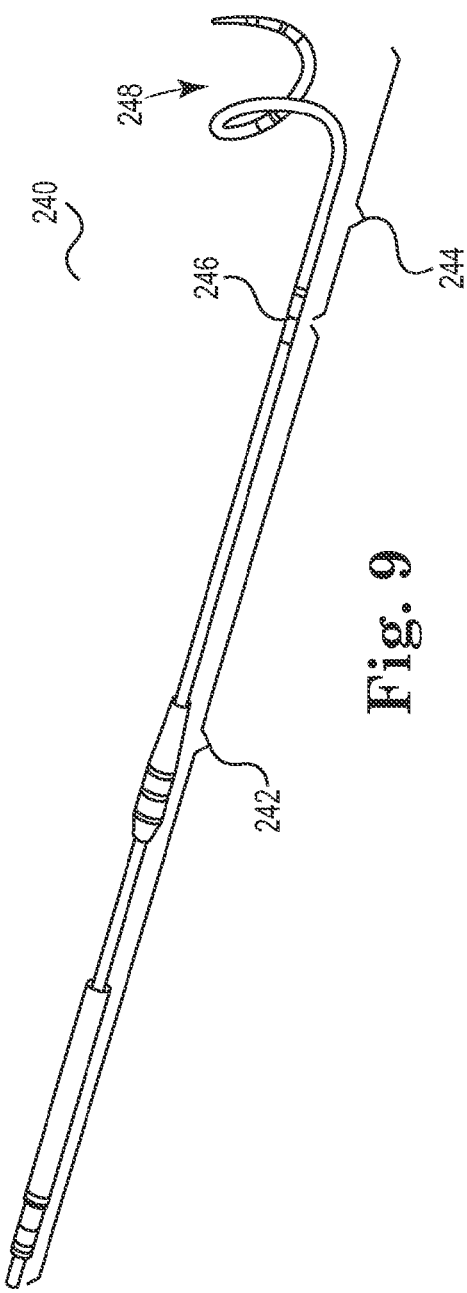
FIG. 9 is a perspective view of a lead, according to one embodiment.

In one example of a lead with design requirements that can be optimized using a coiled conductor having two or more segments, the lead 240 depicted in FIG. 9 has two segments 242, 244 along its length for which different characteristics are required, and a transition point 246 between those segments. In this exemplary lead 240, the proximal segment 242 has a polyurethane body (which has relatively high stiffness in comparison to lead bodies made of other materials), must often meet intracardiac and subcutaneous flexural fatigue requirements, and must often be configured to receive finishing wires and guide wires. As such, it is desirable to have a coiled conductor with a proximal segment that has an I.D. large enough to receive any finishing or guide wires, a minimized pitch and filar count to optimize its flexural fatigue characteristics, and a material or coating that prevents metal ion oxidation of the polyurethane body tubing.

In contrast, the distal segment 244 of this lead has a silicone body and must be capable of being formed into a bias shape such as the spiraled shape 248 as shown in the figure that meets the bias fixation requirements for the distal end and have a minimized diameter to produce the smaller tip geometry necessary for the lead. On the other hand, the distal segment 244 need only meet the intracardiac flexural fatigue requirements and need only be configured to receive guide wires. As such, the distal segment of the coiled conductor, in comparison to the proximal segment, should have a smaller O.D., an increased pitch and filar count to enhance the ability of the coil to be formed into the desired bias shape, and does not need to be configured to prevent metal ion oxidation (since silicone is not susceptible to it).

Given the flexibility provided by the various coiled conductor embodiments and manufacturing methods disclosed herein, a coiled conductor can be manufactured that can satisfy the requirements set forth above to optimize the desired lead characteristics. Similarly, it is understood that the flexibility of the variable coiled segments according to the various embodiments disclosed herein allows for optimization of many different lead requirements.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of constructing a coil conductor of an implantable medical lead, the coil conductor having at least a proximal segment and a distal segment, the method comprising:
winding at least one filars into a coiled configuration over a first section of a mandrel to form the proximal segment, wherein the proximal segment comprises a first outer diameter and a first pitch, the proximal segment ending at a transition point, the at least one filars having a coating thereon during the winding of the proximal segment;
removing the coating from a section of the at least one filars; and
winding the section of the at least one filars from the transition point into a coiled configuration over a second section of the mandrel to form the distal segment, the distal segment comprising a second outer diameter and a second pitch, the distal segment wound from the section such that the at least one filars are uncoated along the distal segment and are coated along the proximal segment
wherein an outside diameter of the first section of the mandrel is different from an outside diameter of the second section of the mandrel.

2. The method of claim 1, wherein removing the coating comprises removing the coating with a laser.

3. The method of claim 1, wherein removing the coating from the section of the at least one filars comprises removing the coating after the proximal segment has been wound.

4. The method of claim 3, wherein and the coating is removed from the section of the at least one filars while the distal segment is being wound.

5. The method of claim 3, wherein the coating is removed from the section of the at least one filars after the distal segment is wound.

6. The method of claim 3, wherein the coating is removed from the section of the at least one filars before the distal segment is wound.

7. The method of claim 1, wherein the second outer diameter is less than the first outer diameter.

8. The method of claim 1, wherein the first pitch is less than the second pitch.

9. The method of claim 8, wherein the proximal segment has different flexural characteristics than the distal segment based at least in part on the first pitch being less than the second pitch.

10. The method of claim 1, wherein:
    winding the proximal segment comprises winding the proximal segment with a plurality of filars, including the at least one filars, and
    the method further comprises removing at least one of the plurality of filars after winding the proximal segment but before winding the distal segment such that the proximal segment comprises more filars than the distal segment.

11. The method of claim 1, further comprising adding at least one more filar to the at least one filars after winding the proximal segment but before winding the distal segment such that the distal segment comprises more filars than the proximal segment.

\* \* \* \* \*